US00PP32767P2

(12) United States Plant Patent
Olesen

(10) Patent No.: US PP32,767 P2
(45) Date of Patent: Jan. 26, 2021

(54) COMPACT FLORIBUNDA ROSE PLANT NAMED 'POULPAL078'

(50) Latin Name: ***Rosa* hybrid**
Varietal Denomination: Poupal078

(71) Applicant: Mogens Nyegaard Olesen, Fredensborg (DK)

(72) Inventor: Mogens Nyegaard Olesen, Fredensborg (DK)

( * ) Notice: Subject to any disclaimer, the term of this patent is extended or adjusted under 35 U.S.C. 154(b) by 0 days.

(21) Appl. No.: 16/602,255

(22) Filed: Sep. 4, 2019

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
CPC ..... A01H 5/02
See application file for complete search history.

(56) References Cited

PUBLICATIONS http://www.poulsenroser.com/assortment/rose-collections/palace/flavian.aspx; Apr. 25, 2020; 1 page.*

* cited by examiner

*Primary Examiner* — Kent L Bell

(57) ABSTRACT

A new garden rose plant of the compact floribunda class which has abundant, light pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal078'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpal078', originated as a single seedling from the stated cross.

The new variety may be distinguished from its male pollen parent and female seed parent primarily by the following characteristics. The male pollen parent plant has ivory white flowers while the new variety has light pink flowers. The female seed parent plant has mauve flowers while the new variety has light pink flowers.

The objective of the hybridization of this rose variety was to create a new and distinct variety with unique qualities, such as:

1. Uniform and abundant light pink, fragrant flowers;
2. Vigorous, but compact growth when propagated on its own roots;
3. Exceptional disease resistance.

This combination of qualities is not present in previously available commercial cultivars of this type, known to the inventor, and distinguish 'Poulpal078' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpal078' was selected in the spring of 2011 by the inventor as a single plant from the progeny of the aforementioned hybridization.

Asexual reproduction of 'Poulpal078' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpal078' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal078'.

Specifically illustrated in the drawing are open flowers, petals detached, sepals detached revealing reproductive flower parts, leaves, and bare stems. Plants shown are 2 years of age.

DETAILED DESCRIPTION OF THE VARIETY

The following is a description of 'Poulpal078',as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah057', U.S. Plant Pat. No. 25,948 are compared to 'Poulpal078' in Chart 1.

CHART 1

| | 'Poulpal078' | 'Poulpah057' |
|---|---|---|
| Petal Count | 65 petals | 60 petals |
| Flower Diameter | 70 mm | 50 mm |
| General Tonality of Flower Color | Open flowers are Red-Purple Group 65C | Red Group 55B and 55C |

FLOWER AND FLOWER BUD

Blooming habit: Continuous.

Flower bud:

*Size*.—Upon opening, 23 mm in length from base of receptacle to end of bud. Bud diameter is 15 mm.

*Bud form*.—Ovoid.

*Bud color*.—As sepals divide petals are Red- Purple Group 63A.

*Sepal inner surface*.—Color: Yellow-Green Group 146D. Surface: Lightly pubescent.

*Sepal outer surface*.—Color: Yellow-Green Group 144A with intonations of Greyed-Purple Group 183A. Texture: Smooth.

*Sepal shape*.—General shape: Subulate. Apex: Cirrhose. Base: Flat at union with receptacle.

*Sepal margin*.—Margins have weak foliaceous appendages on three of the five sepals.

*Sepal size*.—21 mm long, 8 mm wide.

*Receptacle*.—Texture: Smooth. Size: 5 mm in height, 6 mm wide. Color: Yellow-Green Group 144A with intonations of Greyed-Purple Group 183A. Shape: Campanulate.

*Pedicel*.—Surface: Smooth. Length: 26 mm. Diameter: 2 mm on average. Color: Yellow-Green Group 144C with intonations of Greyed-Purple Group 183C. Strength: Strong.

*Peduncle*.—Length: About 3 cm. Diameter: About 3 mm. Color: Yellow-Green Group 144C. Texture: Smooth.

Flower bud development: Flower buds are borne in clusters of 1 to 3 flower buds per stem.

Flower bloom:

*Fragrance*.—Strong perfume.

*Duration*.—The blooms have a duration on the plant of approximately 14 days. Petals fall cleanly away from plant after flowers have fully matured.

*Size*.—Flower diameter is 70 mm when open. Flower depth is 30 mm.

*Flower shape*.—Open cup, very double flower, with petals that curve out from the center.

*Shape of flower, side view*.—The upper portion is flat. The lower portion is flat concave.

Petalage: Under normal conditions, flowers have about 65 petals.

General tonality of flower: Open flowers are Red-Purple Group 65C.

Petal color:

*Upon opening, outer petals*.—Upper surface: Red Group 49B. Lower surface: Red-Purple Group 65C splashed with Red-Purple Group N66C.

*Upon opening, inner petals*.—Upper surface: Red Group 49B. Lower surface: Red-Purple Group 65C splashed with Red-Purple Group N66C.

*Basal petal spots, upon opening*.—Upper surface: Yellow Group 4D. Lower surface: Yellow Group 5B.

*After opening*.—Outer and inner petals have same coloration as upon opening.

Petals:

*Petal reflex*.—Partially reflexed.

*Margin*.—Entire and uniform. Moderate undulations.

*Shape*.—Very broad and elliptic. Apex shape: Rounded. Base shape: Rounded.

*Size*.—35 mm (l)×32 mm (w).

*Texture*.—Smooth.

*Thickness*.—Average.

Petaloids:

*Size*.—10 mm (l) by 9 mm (w).

*Quantity*.—About 12.

*Shape*.—Irregular shaped, with rounded base and apex.

*Margins*.—Undulated, with occasional cleft.

*Color*.—The upper surface is Red Group 49B. Lower surface is Red-Purple Group 65C splashed with Red-Purple Group N66C. At the petaloid base intonations of Yellow Group 4D on the lower and upper surface.

Reproductive flower parts:

*Pollen*.—None observed.

*Anthers*.—Size: 2 mm in length. Color: Yellow-Orange Group 14C. Quantity: 42 on average.

*Filaments*.—Color: Yellow-Orange Group 21B. Length: 8 to 10 mm.

*Pistils*.—Length: 6 mm. Quantity: 25 on average.

*Stigmas*.—Color: Yellow-White Group 158A.

*Styles*.—Color: Greyed-Red Group 181B.

*Location of stigmas*.—Inferior in location relative to the length of the filaments and the height of the anthers.

*Hips*.—None Observed.

PLANT

Plant growth: Upright, bushy. Plants are 40 cm in height, and 35 cm wide.

Stems:

*Color of juvenile growth*.—Yellow-Green Group 144B.

*Color of mature growth*.—Yellow-Green Group 144A.

*Length*.—Canes are about 15 cm from the base of the plant to the flowering portion.

*Diameter*.—About 4 mm.

*Internodes*.—On mature canes about 40 mm between nodes.

*Surface texture*.—Young wood: Smooth. Older wood: Smooth.

Long prickles:

*Incidence*.—3 to 4 prickles per 10 cm of stem.

*Size*.—Average length of prickles on mature stems is 6 mm.

*Shape*.—Upper portion is linear. Lower portion is concave.

*Color*.—Juvenile prickles: Greyed-Red Group 179C. Mature prickles: Greyed-Red Group 179C.

Plant foliage:

*Compound leaf*.—110 mm (l)×95 mm (w).

*Quantity*.—2 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 144A. Lower side: Yellow-Green Group 144B.

Plant leaves and leaflets:

*Stipules*.—Size: 14 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 3 mm. Upper surface color: Yellow-Green Group 144C with intonations of Greyed-Red Group 180D. Lower surface color: Yellow-Green Group 144B.

*Rachis*.—Length: 40 mm. Diameter: 2 mm. Upper surface color: Yellow-Green Group 144C. Lower surface color: Yellow-Green Group 144B.

*Leaflet*.—Quantity: Normally 5 leaflets. Margins: Double serrated. Size: Terminal leaflets are about 48 mm long, 35 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: Susceptible to any insect pest normally associated with the species.

We claim:

1. A new and distinct variety of rose plant of the Compact Floribunda rose class named 'Poulpal078', substantially as illustrated and described herein, due to its abundant light pink flowers, disease resistance, and extended period of bloom.

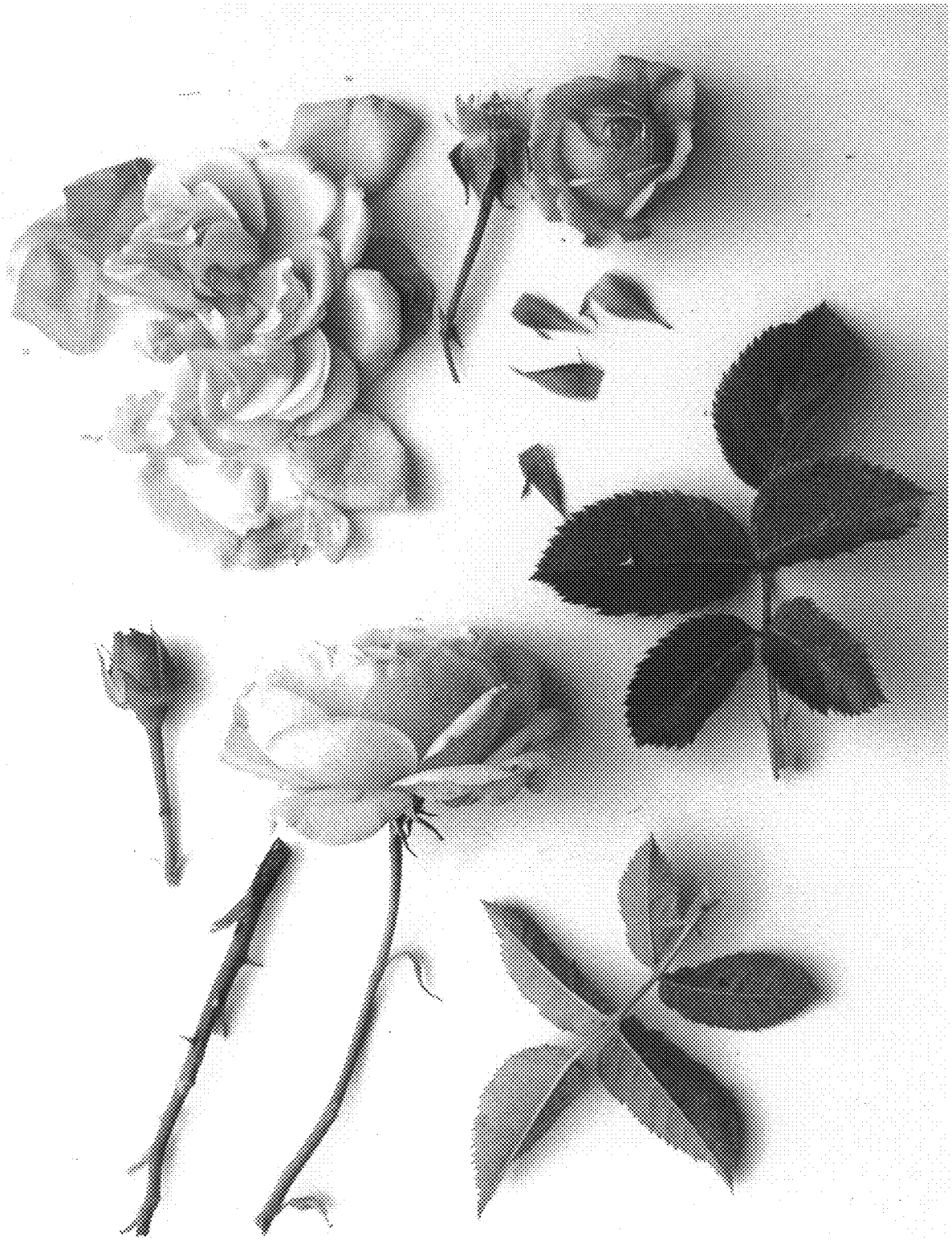

* * * * *